Figure 1:
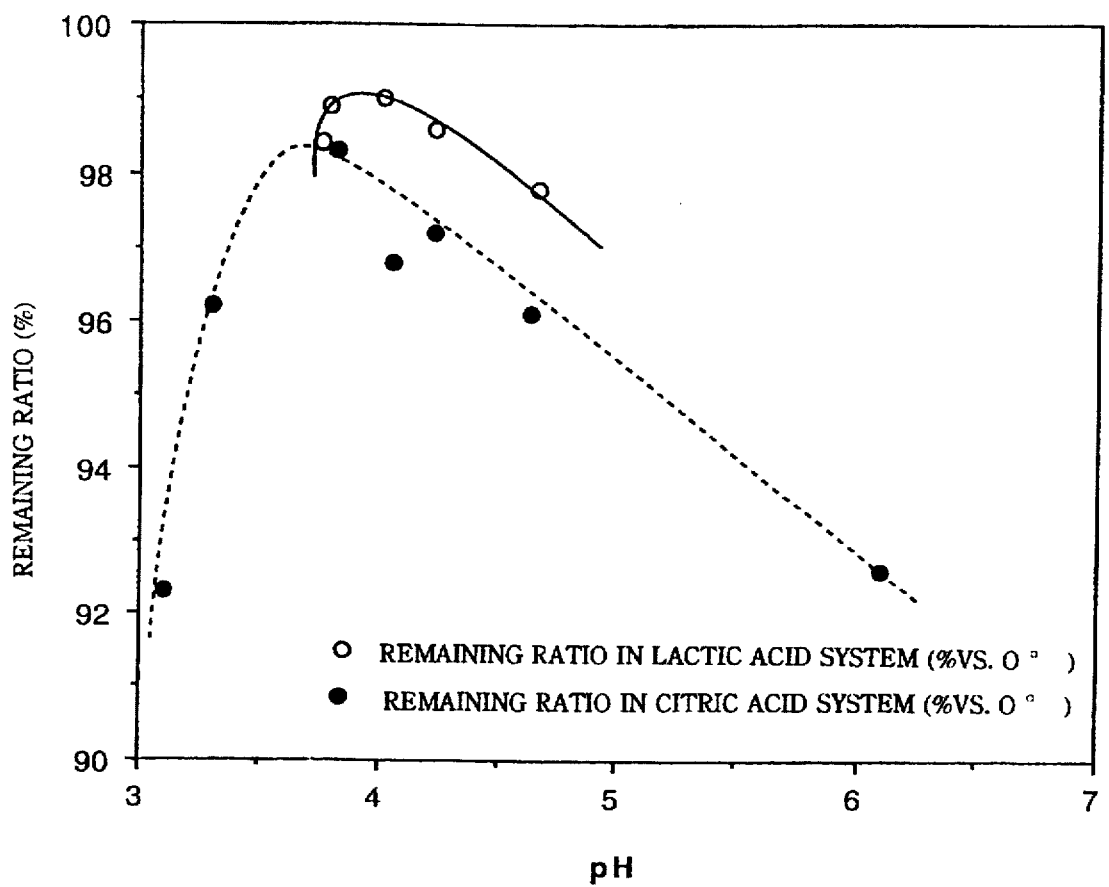

United States Patent [19]
Igarashi et al.

[11] Patent Number: 5,800,827
[45] Date of Patent: Sep. 1, 1998

[54] DISINFECTANT COMPOSITION

[75] Inventors: Yasuo Igarashi; Takashi Suzuki; Tomoko Kimura; Akira Motoyama; Rina Fukuhara; Atsuko Torii, all of Yokohama, Japan

[73] Assignee: Shiseido Co., Ltd., Tokyo, Japan

[21] Appl. No.: 544,633

[22] Filed: Oct. 18, 1995

[30] Foreign Application Priority Data

Oct. 21, 1994 [JP] Japan .................. 6-282976

[51] Int. Cl.⁶ .................. A01N 31/00; A01N 37/12
[52] U.S. Cl. .................. 424/405
[58] Field of Search .................. 424/405

[56] References Cited

U.S. PATENT DOCUMENTS

| | | | |
|---|---|---|---|
| 4,900,721 | 2/1990 | Bansemir et al. | 424/49 |
| 4,942,041 | 7/1990 | Guhl et al. | 424/613 |
| 5,004,757 | 4/1991 | Boucher | 514/694 |
| 5,017,617 | 5/1991 | Kihara et al. | 514/635 |
| 5,030,659 | 7/1991 | Bansemir et al. | 514/635 |
| 5,167,950 | 12/1992 | Lins | 424/47 |
| 5,334,338 | 8/1994 | Hoag et al. | 424/402 |

FOREIGN PATENT DOCUMENTS

| | | |
|---|---|---|
| A 375827 | 7/1990 | European Pat. Off. |
| 2187097 | 9/1987 | United Kingdom |
| A 8501876 | 5/1985 | WIPO |
| A 9512395 | 5/1995 | WIPO |

OTHER PUBLICATIONS

WPI Abstract No. AN 91-321575 & JP A-03-215411.

*Primary Examiner*—Amy Hulina
*Attorney, Agent, or Firm*—Ronald R. Snider

[57] ABSTRACT

A disinfectant composition contains ethyl alcohol with a concentration of not lower than 50% by weight, chlorhexidine, and an organic acid. Even when the concentration of ethyl alcohol is not lower than 50% by weight, chlorhexidine can be compounded therein very stably.

2 Claims, 1 Drawing Sheet

DISINFECTANT COMPOSITION

FIELD OF THE INVENTION

The present invention relates to a disinfectant composition and, in particular, to stabilization of chlorhexidine in an ethyl alcohol base.

BACKGROUND OF THE INVENTION

Chlorhexidine is a compound which is formally called 1,1-hexamethylenebis [5-(4-chlorophenyl) biguanide]. Due to its continuous and wide disinfecting action, this compound has been compounded as a germicidal prophylactic agent for diseases, an antiseptic, a deodorant, or an anti-inflammatory agent in drugs for pyorrhea, disinfectants, and the like.

Also, as hospital infection within a hospital has often been reported in paper recently, a demand for compounds such as chlorhexidine which can be used in a wide range of disinfection is expected to increase.

In the hospital infection within a hospital, it has been reported that there are cases where an infection is transferred from one patient to another patient by way of doctors and nurses. Accordingly, it is necessary for them to disinfect their hands and fingers completely and rapidly after treating or taking care of one patient before treating or taking care of another patient.

Therefore, various kinds of quick-drying disinfectants which are mainly composed of ethyl alcohol have recently been studied.

However, it is insufficient for quick-drying ethyl alcohol alone to disinfect hands and fingers. Accordingly, chlorhexidine, which has a sufficient germicidal action, may be added to ethyl alcohol. It has nevertheless been known that, while chlorhexidine is stable in aqueous solution systems since it is inherently water-soluble, its stability is low in ethyl alcohol bases.

On the other hand, in order to maintain quick-dryness and germicidal power, it is preferable for the ethanol content in such a mixture to be at the same level as that in disinfectant ethanol. Though there is a demand for development of disinfectants in which chlorhexidine is stably compounded while maintaining the germicidal property and quick-dryness, no products have been found sufficiently satisfactory.

SUMMARY OF THE INVENTION

In view of the foregoing problems of the prior art, an object of the present invention is to provide a disinfectant composition in which chlorhexidine is stably compounded in a highly concentrated ethyl alcohol solution.

As a result of diligent studies of the inventors to attain the above-mentioned object, it has been found that chlorhexidine can stably be compounded in a highly concentrated ethyl alcohol solution when an organic acid is added thereto and thus the present invention has been accomplished.

Namely, the disinfectant composition in accordance with the present invention is characterized in that it contains ethyl alcohol with a concentration of not lower than 50% by weight, chlorhexidine, and an organic acid.

Preferably, the system of the present invention has a pH from 3 to 5.

Preferably, the organic acid is selected from the group consisting of organic acids having a carbon number from 2 to 16.

Preferably, the organic acid is soluble to an ethyl alcohol solution having a concentration of not lower than 50% by weight and able to adjust the pH of the system from 3 to 5.

Examples of such an organic acid include acetic acid, lactic acid, maleic acid, malic acid, citric acid, salicylic acid, myristic acid, and palmitic acid. Among them, lactic acid and citric acid are preferable in particular.

Also, other ingredients may be compounded in the disinfectant composition in accordance with the present invention. For example, glycyrrhizinic acid and its derivatives; drugs such as vitamin E, vitamin E acetate, and vitamin B6; water-soluble polymers such as xanthan gum, dextrin, hydroxyethyl cellulose, hydroxymethyl cellulose, methyl cellulose, carrageenan, and carboxymethyl cellulose; and the like may be compounded.

Further, nonionic surfactants and, in order to increase skin-protecting power, urea or the like may be compounded so as to impart a cleaning effect to the composition.

In one aspect, the present invention provides a disinfectant composition used for disinfecting hands and fingers.

In another aspect, the present invention provides a method of disinfecting fingers and hands in which the disinfectant composition for disinfecting fingers and hands are used.

BRIEF DESCRIPTIONS OF THE DRAWING

FIG. 1 is a graph explaining the relationship between the ratio of remaining chlorhexidine in citric acid and lactic acid systems and the pH in these systems.

EXAMPLES

In the following, preferable examples of the present invention will be explained. However, the present invention is not restricted to these examples.

Stabilty of Chlorhexidine vs. Ethyl Alcohol Concentration

First, the inventors studied the relationship between ethyl alcohol concentration and stability of chlorhexidine.

The aqueous solutions with the ethyl alcohol concentrations listed below and a chlorhexidine content of 0.2% W/V were prepared and then stored for one month each at 50° C. and 0° C. Thereafter, chlorhexidine therein was quantitatively determined. The remaining ratio is calculated as the ratio of the amount of chlorhexidine remaining at 50° C. with respect to that at 0° C. which is taken as 100%.

The results are shown in TABLE 1.

TABLE 1

| Ethyl alcohol conc. | 0 | 10 | 20 | 30 | 40 | 50 | 60 | 70 | 86 |
|---|---|---|---|---|---|---|---|---|---|
| Remaining ratio | 100 | 95 | 81 | 75 | 69 | 65 | 58 | 53 | 48 |

On the other hand, when quick-dryness and germicidal power are expected to be improved by ethyl alcohol, the concentration thereof should be not lower than 50% by weight or, more preferably, not lower than 70% by weight.

Accordingly, the inventors studied how to improve the stability of chlorhexidine in highly concentrated ethyl alcohol.

Stability vs. Various Additives

In order to stabilize chlorhexidine in ethyl alcohol, the inventors added various materials, which hardly affected human bodies, to a mixture of chlorhexidine and ethyl alcohol.

The concentration of ethyl alcohol in the mixture was 80% V/V, while each additive was added thereto so as to attain a content of 0.1% W/V. The stability of chlorhexidine in the resulting mixture was evaluated in the same manner as noted above.

The results are shown in TABLE 2.

TABLE 2

| Additive | Remaining ratio |
| --- | --- |
| Allantoin | 92% |
| Glycine | 91% |
| Citric acid | 99% |
| Lactic acid | 99% |
| Butyl hydroxy toluene | 91% |
| Tocopherol | 94% |

As shown in TABLE 2, it was found that, among various additives, organic acids having a carbon number from 2 to 16 such as citric acid and lactic acid had a remarkably high stability—imparting action.

Stability vs. System pH Changed by Addition of Organic Acid

Next, in a system having an ethyl alcohol concentration of 80% by weight, the stability of chlorhexidine was evaluated while the pH of the system was changed by the amount of organic acids being added thereto. The stability was evaluated in the same manner as noted above. Since it was difficult to directly determine the pH in a highly concentrated alcohol system, purified water, which had once been boiled and cooled, was added to 5 g of the sample liquid to yield a solution having a whole amount of 50 g. While thus obtained solution was stirred at room temperature, the pH thereof was determined.

The results are shown in FIG. 1.

As clearly shown in this drawing, advantageous effects were recognized at the region where pH was from 3 to 5. In particular, the optimum region for stabilizing chlorhexidine existed near a pH of 4.

As a result, it is understood that citric acid, lactic acid, and the like, as noted above, are preferable as compounds which can adjust, with a small amount thereof being added, the pH of the solution having an ethyl alcohol concentration of not lower than 50% by weight from 3 to 5.

In the following, more specific compounding examples of disinfectant compositions in which chlorhexidine was stably compounded will be described.

| COMPOUNDING EXAMPLE 1 | |
| --- | --- |
| Hibitane gluconate liquid (with 20% chlorhexidine) | 1.0 g |
| Cationic surfactant | 0.02 |
| Glyceryl triisooctanate | 0.4 |
| Citric acid | 0.1 |
| Purified water | 18.0 |
| Ethanol | q.s. to make 100 ml |
| COMPOUNDING EXAMPLE 2 | |
| Hibitane gluconate liquid (with 20% chlorhexidine) | 1.0 g |
| Cationic surfactant | 0.02 |
| Glyceryl triisooctanate | 0.4 |
| Lactic acid | 0.1 |
| Purified water | 18.0 |
| Ethanol | q.s. to make 100 ml |

Both disinfectant compositions in accordance with these compounding examples exhibited an excellent stability.

As explained in the foregoing, in the disinfectant composition in accordance with the present invention, as an organic acid is added thereto, chlorhexidine can be compounded therein very stably even when the ethyl alcohol concentration therein is not lower than 50% by weight, thereby satisfying the germicidal property and quick-dryness of the disinfectant.

What is claimed is:

1. A disinfectant composition consisting essentially of ethyl alcohol with a concentration of not lower than 50% by weight of said composition, chlorhexidine, and an organic acid, wherein said organic acid is at least one of lactic acid and citric acid, and said composition has a pH of from 3 to 5.

2. A disinfectant composition consisting of ethyl alcohol with a concentration of not lower than 50% by weight of said composition, chlorhexidine, and an organic acid, wherein said organic acid is at least one of lactic acid and citric acid, said composition having a pH of from 3 to 5, and wherein at least one other compound selected from the group consisting of glycyrrhizinic acid and its derivatives, vitamine E, vitamine E acetate, vitamin B , xanthan gum, dextrin, hydroxyethyl cellulose, hydroxymethyl cellulose, methyl cellulose, carrageenan, and carboxymethyl cellulose is/are further compounded.

* * * * *